United States Patent [19]

Mariani et al.

[11] Patent Number: 4,508,730

[45] Date of Patent: * Apr. 2, 1985

[54] 1,7-DIHYDRO-PYRROLO[3,4-E][1,4]DIAZE-PIN-2(3H)-ONE DERIVATIVES A PROCESS FOR PREPARING THEM AND THEIR USE AS ANTICONVULSANT AND ANTI-ANXIETY AGENTS

[75] Inventors: Luigi Mariani; Giorgio Tarzia, both of Milan, Italy

[73] Assignee: Gruppo Lepetit S.p.A., Italy

[*] Notice: The portion of the term of this patent subsequent to Sep. 6, 2000 has been disclaimed.

[21] Appl. No.: 521,774

[22] Filed: Aug. 9, 1983

[30] Foreign Application Priority Data

Sep. 8, 1982 [GB] United Kingdom ............. 8225582

[51] Int. Cl.³ ..................... A61K 31/55; C07D 487/04
[52] U.S. Cl. ............................. 514/218; 260/239.3 B
[58] Field of Search ................ 260/239.3 B; 424/274

[56] References Cited

U.S. PATENT DOCUMENTS

| 4,022,766 | 5/1977 | Fontanella et al. | 260/239.3 B |
| 4,391,817 | 7/1983 | Mariani et al. | 260/239.3 B |
| 4,402,970 | 9/1983 | Mariani et al. | 260/239.3 B |

Primary Examiner—Robert T. Bond
Attorney, Agent, or Firm—William J. Stein; Stephen L. Nesbitt; Raymond A. McDonald

[57] ABSTRACT 1,7-Dihydro-pyrrolo[3,4-e][1,4]diazepin-2(3H)-one derivatives of the formula

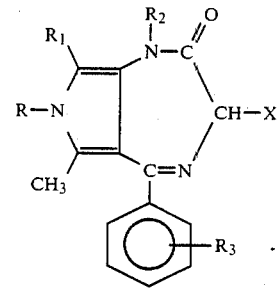

wherein R is $(C_{1-4})$alkyl, $R_1$ stands for hydrogen, methyl, ethyl, phenyl, bromo, chloro or nitro, $R_2$ is hydrogen or $(C_{1-4})$alkyl, $R_3$ represents hydrogen, chloro, fluoro, bromo, trifluoromethyl and methoxy, and X is

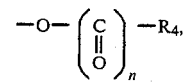

wherein n is zero or 1, or $-NH-R_4$ wherein $R_4$ represents a substituted or unsubstituted alkyl, alkenyl, cycloalkyl, or phenyl group.

The novel compounds are useful as anticonvulsant and anti-anxiety agents.

Also encompassed by the present invention are the process for preparing the novel pyrrolodiazepines and the pharmaceutical compositions containing them.

10 Claims, No Drawings

1,7-DIHYDRO-PYRROLO[3,4-E][1,4]DIAZEPIN-2(3H)-ONE DERIVATIVES A PROCESS FOR PREPARING THEM AND THEIR USE AS ANTICONVULSANT AND ANTI-ANXIETY AGENTS

The present invention refers to a 1,7-dihydro-pyrrolo[3,4-e][1,4]diazepin-2(3H)-one derivative of the following formula I

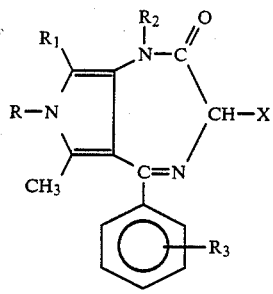

wherein

R represents methyl, ethyl, propyl, 1-methylethyl, butyl, 1-methylpropyl, 2-methylpropyl and 1,1-dimethylethyl;

$R_1$ stands for hydrogen, methyl, ethyl, phenyl, bromo, chloro or nitro;

$R_2$ is hydrogen, methyl, ethyl, propyl, 1-methylethyl, butyl, 1-methylpropyl, 2-methylpropyl and 1,1-dimethylethyl;

$R_3$ represents hydrogen, chloro, fluoro, bromo, trifluoromethyl and methoxy, and X is

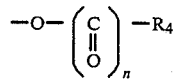

wherein n is 0 or 1 or $-NH-R_4$ and $R_4$ represents a straight or branched alkyl or alkenyl group which may contain up to 12 carbon atoms, which may be unsubstituted or substituted with one or more groups independently selected from ($C_{1-4}$)alkoxy, halogen, carboxy, carbo-($C_{1-4}$)alkoxy, amino, mono- or di-($C_{1-4}$)alkylamino, ($C_{2-4}$)alkanoylamino, benzoylamino, phthalimido, carbamyl, ($C_{1-4}$)alkylcarbamyl, carboxy-($C_{1-4}$)alkylcarbamyl, carbalkoxy-($C_{1-4}$)alkylcarbamyl, and phenylcarbamyl, a ($C_{5-8}$)cycloalkyl group which may be unsubstituted or substituted with one or two groups independently selected from ($C_{1-4}$)alkyl, hydroxy, halogen, carboxy, and carbo($C_{1-4}$)alkoxy, or a phenyl group which may be unsubstituted or substituted with 1 to 3 groups independently selected from ($C_{1-4}$)alkyl, ($C_{1-4}$)alkoxy, ($C_{3-8}$)cycloalkyl, amino, mono- or di-($C_{1-4}$)alkylamino, phenyl, trifluoromethyl and halogen; with the proviso that when simultaneously $R_1$ is hydrogen, methyl, ethyl or phenyl and X is an

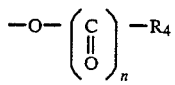

group wherein n is 1, $R_4$ cannot represent methyl.

The present invention further encompasses the pharmaceutically acceptable acid addition salts of the aforesaid compounds.

Illustrative of the pharmaceutically acceptable acid addition salts of the compounds of the present invention are salts with inorganic acids such as, for example, hydrochloric, hydrobromic, sulfuric, phosphoric and like acids; and with organic carboxylic or sulfonic acids such as, for example, acetic, propionic, glycolic, malonic, succinic, tartaric, citric, benzoic, phenylacetic, anthranilic, cinnamic, methansulfonic and p-toluensulfonic acid.

The new pyrrolodiazepines of the present invention are useful as anticonvulsant and anti-anxiety agents.

A preferred group of compounds comprises those compounds of formula I wherein R is methyl, $R_1$ is hydrogen, $R_2$ is as defined above, $R_3$ represents hydrogen, chloro, fluoro or bromo, and X is as defined above.

A most preferred group of compounds comprises those compounds of formula I wherein R is methyl, $R_1$ is hydrogen, $R_2$ is hydrogen or methyl, $R_3$ stands for hydrogen or chloro and X is as defined above.

1,4-Diazepines fused on a pyrrole ring are described in Belgian Pat. No. 826,925. These compounds differ structurally from those of the present invention in the presence of a methylene group instead of a $>CH-X$ group at the 3-position.

The new compounds of the present invention are prepared starting from a 3-hydroxy derivative of formula II

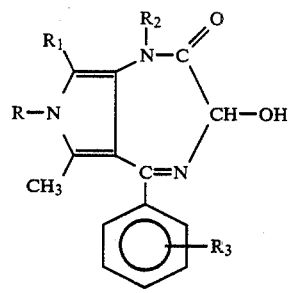

wherein R, $R_2$ and $R_3$ are as defined above and $R_1$ is hydrogen, methyl, ethyl or phenyl, by common substitution reactions of the 3-positioned hydroxy group followed, when a compound of formula I is desired wherein $R_1$ is bromo, chloro, or nitro, by bromination, chlorination or nitration of the thus obtained compounds of formula I wherein $R_1$ is hydrogen.

In particular, when a compound of formula I is desired wherein X is an

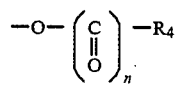

group wherein n is 1, it may be prepared by common O-acylation procedures through reaction of the starting compound of formula II, wherein R, $R_2$ and $R_3$ are as defined above and $R_1$ is hydrogen, methyl, ethyl or phenyl, with a suitably selected acyl halogenide or anhydride of formula

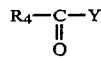

wherein R4 is as defined above and Y is a halogen atom, preferably chlorine or bromine, or the group

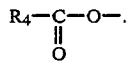

The acylating agent R4COY is employed in about equimolar proportion to or in a slight excess over the 3-hydroxy derivative II, and a base is frequently added either to tie up the hydrohalic acid which forms during the course of the reaction, or, when an anhydride is employed, to catalyze the alcoholysis. Aqueous alkali can be used but tertiary organic nitrogen bases are preferably employed. Among the amines which are very useful to this purpose, there are pyridine, picolines and tri-lower alkyl amines, typically triethylamine. The reaction is generally carried out in the presence of an inert organic solvent such as aromatic hydrocarbons, typically benzene, toluene and xylene, lower halogenated aliphatic hydrocarbons such as methylene chloride, chloroform and carbon tetrachloride and the like. However, when pyridine or picolines are employed as the tertiary organic nitrogen bases, they may also act as the reaction solvents and the use of an additional solvent can be avoided. The O-acylation reaction may easily proceed at room temperature, however it is generally preferred to heat or reflux the reaction mixture in order to speed up the reaction rate. Depending on the temperature employed, the reaction which can be monitored by thin-layer chromatography is complete in about 1 to about 6 hours. At the end of the reaction, the obtained ester of formula I is recovered by conventional procedures, which involve evaporation of the solvent and washing of the raw residue with water, and is purified for instance by crystallization from a suitable crystallization solvent.

According to a preferred embodiment, when a compound of formula I is desired wherein X stands for an

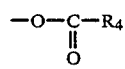

group wherein R4 is a straight or branched alkyl or alkenyl group substituted at position 2 or 3 with a carboxy, carbo-($C_{1-4}$)alkoxy, carbamyl, ($C_{1-4}$)alkylcarbamyl, carboxy-($C_{1-4}$)alkylcarbamyl, carbo-($C_{1-4}$)alkoxy-($C_{1-4}$)alkylcarbamyl or phenylcarbamyl group, a cyclic anhydride is employed. In this case mono-esterified dicarboxylic acids are obtained. As an example the use of succinic, glutaric or maleic anhydride yields compounds of formula I wherein X stands for an

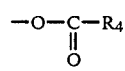

group wherein R4 is a 2-carboxy-ethyl, 3-carboxy-propyl, or 2-carboxy-ethenyl group respectively. If desired, the free carboxy group of the thus obtained compound of formula I may then be transformed, according to conventional esterification or amination procedures, into a carbalkoxy, carbamyl or substituted carbamyl group as seen above.

The compounds of formula I thus obtained wherein R, $R_2$, and $R_3$ are as defined above, X stands for an

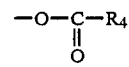

group and $R_1$ is hydrogen may then be converted into the corresponding compounds of formula I wherein $R_1$ is chloro, bromo or nitro through chlorination, bromination or nitration of position 8.

These reactions are easily carried out according to the usual procedures known to any person skilled in the art. In particular these reactions are carried out at low temperature, preferably comprised between $-65°$ C. and $-40°$ C., and in the presence of an organic solvent which does not interfere with the course of the reaction, such as for instance methylene chloride, chloroform, ethyl ether, carbon disulfide, methyl alcohol and the like, using a suitably halogenating or nitrating agent. As for the chlorination, the reaction proceeds with optimum yields using sulphuryl chloride as the chlorinating agent, however, other different chlorinating agents can be employed such as N-chlorosuccinimide, chlorine, and phosphorous pentachloride; analogously for bromination, while according to the usual methods bromine is preferred, other agents, such as N-bromosuccinimide, may advantageously by employed. As for the nitration, a nitronium salt such as nitronium fluoborate or nitronium trifluoromethansulfonate, is a particularly effective nitrating agent.

Compounds of formula I wherein X stands for an

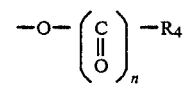

or $-NHR_4$ group wherein n is zero, are easily prepared by converting the corresponding 3-hydroxy derivative of formula II wherein R, $R_2$, and $R_3$ are as defined above and $R_1$ is hydrogen, methyl, ethyl or phenyl, into the more reactive 3-chloro derivative III

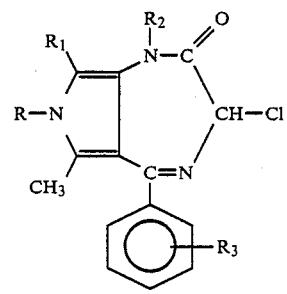

followed by replacement of the chloro atom with an $-OR_4$ or $-NHR_4$ group. The conversion of the 3-hydroxy derivative II into the corresponding chloride III is easily accomplished by the use of an inorganic acid chloride such as $SOCl_2$, $PCl_3$, $PCl_5$, $POCl_3$ etc.

The reaction simply occurs by contacting the 3-hydroxy derivative II and the chlorinating agent for a few hours at room temperature. Recovery of the 3-chloro intermediate is then carried out either by precipitating the raw product by the addition of a non-solvent such as for instance diethyl ether, or by concentrating the reaction mixture to dryness and washing the residue with a suitable organic solvent, such as diethyl ether, that does not solubilize the chloro derivative. Reaction of the obtained intermediate III with a compound of formula $HOR_4$ or $H_2NR_4$, affords the desired end products of formula I wherein R, $R_2$ and $R_3$ are as defined above, X is an

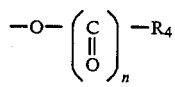

or $-NHR_4$ group wherein n is zero, and $R_1$ is hydrogen, methyl, ethyl or phenyl. This second step is generally carried out in the presence of a hydrogen chloride acceptor and an organic solvent. In some instances however the reactants of formula $HOR_4$ or $H_2NR_4$ may act as the reaction solvents or as the hydrogen halide acceptors. When an organic solvent is employed, it is preferably selected among lower aliphatic halogenated hydrocarbons, such as methylene chloride or chloroform. Recovery and purification of the obtained product are carried out as known in the art. Also in this case, if a compound of formula I is desired wherein X is an

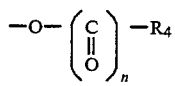

or $-HNR_4$ group wherein n is zero, and $R_1$ is chloro, bromo or nitro, it may be prepared by chlorination, bromination or nitration of the corresponding compound of formula I wherein $R_1$ is hydrogen, by following the procedure seen above.

The starting compounds of formula II are prepared from a 3-aroyl-4-aminopyrrole compound of formula IV through a 7-step synthesis which is briefly illustrated in the following Chart:

Chart

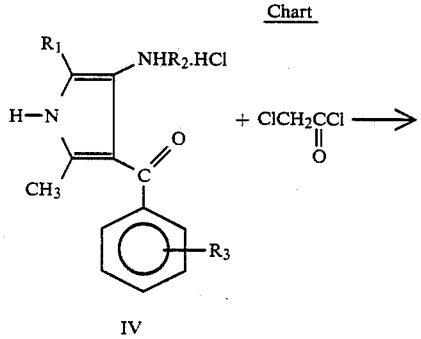

IV

-continued

Chart

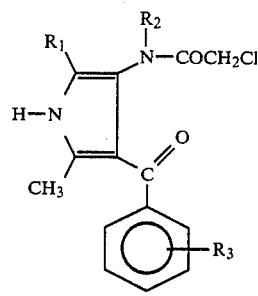

V

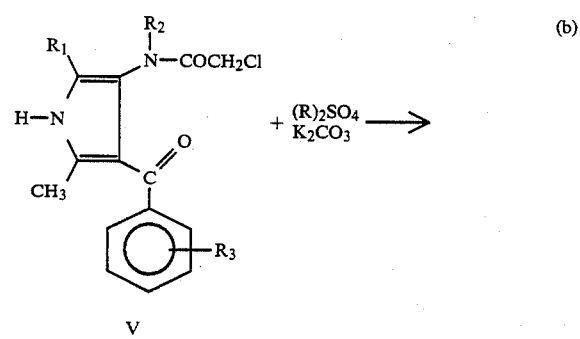

(b)

V

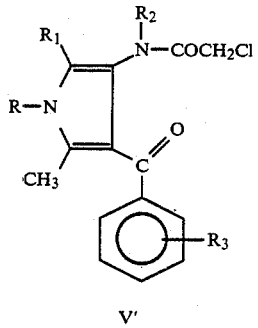

V'

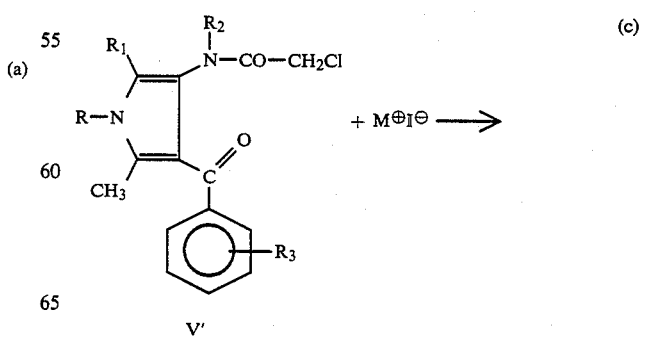

(c)

V'

-continued
Chart 5
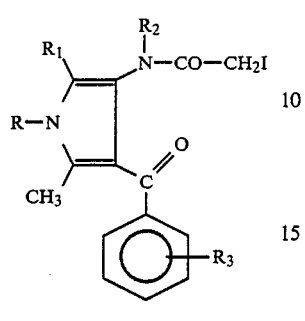
VI
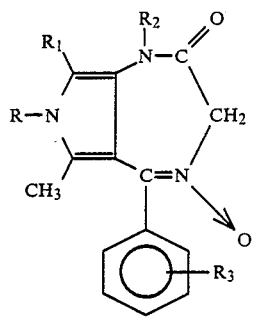
VIII
(d)
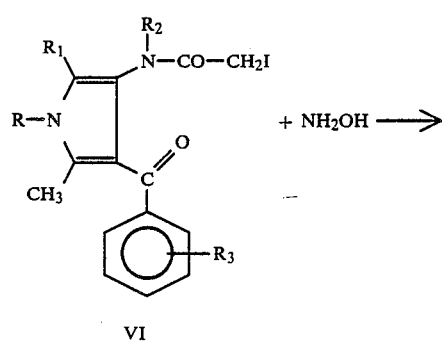
VI + NH₂OH ⟶
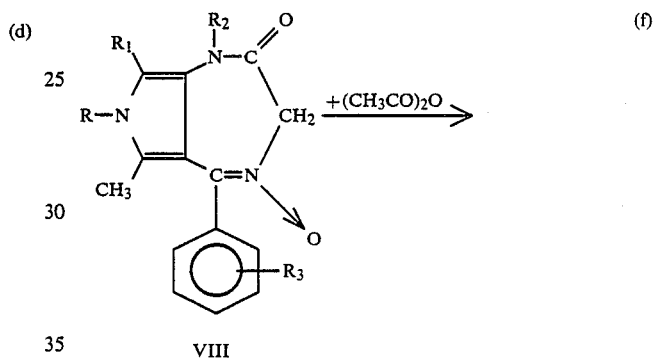
VIII + (CH₃CO)₂O ⟹
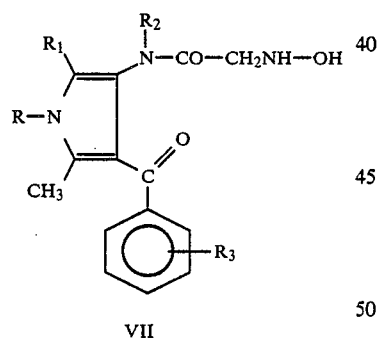
VII
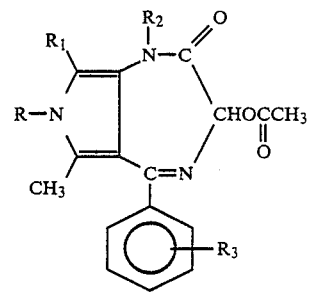
IX
(e)
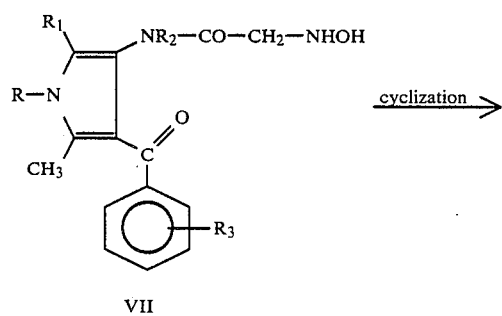
VII  cyclization ⟶
(g)
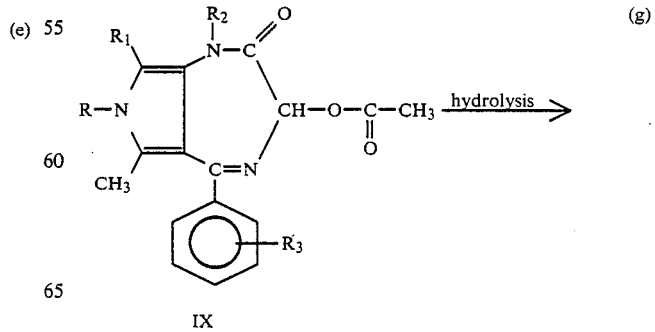
IX  hydrolysis ⟶

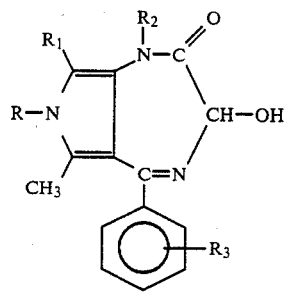

II

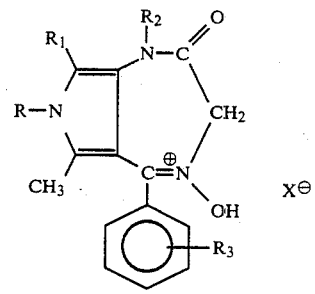

X

According to the first step reported in the preceding Chart, the chloroacetamide derivatives V are prepared through reaction of chloroacetic acid chloride with a 3-aroyl-4-aminopyrrole compound of formula IV wherein $R_1$, $R_2$, and $R_3$ have the same meanings as above.

In their turn, the 3-aroyl-4-aminopyrroles of formula IV are obtained by reacting an α-aminonitrile of formula

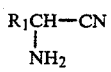

with a β-diketone of formula

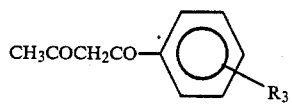

and optionally alkylating the amino nitrogen atom of the thus obtained 3-aroyl-4-aminopyrrole wherein $R_2$ is hydrogen according to conventional procedures. According to step (b) the chloroacetamide derivative V is alkylated at the pyrrole nitrogen atom by means of a dialkylsulfate $(R)_2SO_4$ in the presence of potassium carbonate to give the chloroacetamide derivative V' which is then converted into the corresponding iodoacetamide derivative VI through reaction with an alkali metal iodide in ethanol or acetone according to the Finkelstein reaction.

The iodoacetamide derivative VI thus obtained is then reacted with hydroxylamine to give the N-(4-aroyl-5-methyl-(1H)-pyrrol-3-yl)2hydroxylaminoacetamide VII. In the actual practice this step is carried out by reacting the iodoacetamide derivative with an excess of hydroxylamine, preferably prepared in situ by adding an alkali metal hydroxide to an aqueous solution of hydroxylamine hydrochloride, in a lower alkanol. The intermediate hydroxylaminoacetamide VII is then cyclized to N-oxide as described in step (e). Said cyclization passes through two steps. In the first one, the hydroxyalminoacetamide derivative is converted to an intermediate diazepinum salt of formula X by heating, and preferably refluxing, a suspension of the hydroxylaminoacetamide derivative VII in a lower alkanol in the presence of a strong acid HX, typically hydrochloric, sulfuric, methanesulfonic and the like acids. In the second step, the intermediate diazepinum salt, is transformed into the N-oxide VIII by treatment with aqueous bases such as alkali metal hydroxides or carbonates aqueous solutions.

Rearrangement of the N-oxide VIII with acetic anhydride smoothly takes place by suspending the N-oxide VIII in acetic anhydride. The resulting 3-acetoxy derivative IX is then submitted to mild alkaline hydrolysis yielding the desired starting compounds of formula II.

Furthermore, when a starting compound of formula II is desired wherein $R_2$ is a lower alkyl group, it may be prepared also starting from a 3-aroyl-4-aminopyrrole of formula IV wherein $R_2$ is hydrogen, and submitting the chloroacetamide derivative V or the 3-acetoxy intermediate IX or the N-oxide VIII, obtained by following the process described above, to common alkylation procedures before further processing these intermediates as seen above.

The novel compounds of the present invention possess anticonvulsant and anti-anxiety activity. To evaluate the anticonvulsant activity the compounds of the present invention have been submitted to the antipentylenetetrazole bioassay in mice. The experiments have been carried out by following essentially the methodology described by Berger in J. Pharm. Exptl. Ther. 104, 468, (1952). More particularly, a fatal dose of pentylenetetrazole (140 mg/kg s.c.) was administered to groups of ten mice each, treated, 30 minutes before the administration of the convulsant agent, with a selected dose (100 mg/kg) of the potential anticonvulsant compound. One of these groups, the "control" group, did not receive the anticonvulsant but only the convulsant agent. Since the animals of the control group died within 30 minutes, the effectiveness of the compounds tested was expressed as the number of animals of the group which were still alive two hours after the administration of pentylenetetrazole, out of the total number of animals of the group (10). In this experiment the compounds of examples 1,2,8, 9, 10, 11, 13, 14, 15, 16, and 17 were fully effective giving a 100% protection against pentylenetetrazole. Moreover, the compounds of examples 9 and 17 were tested at lower, different doses, in order to calculate the corresponding $ED_{50}$, i.e. the dose at which 50% of the treated animals are protected. The results obtained in these experiments are reported in the following Table A:

TABLE A

| Compound of example No. | $ED_{50}$ mg/kg/i.p. |
|---|---|
| 9 | 5 |

TABLE A-continued

| Compound of example No. | ED$_{50}$ mg/kg/i.p. |
| --- | --- |
| 17 | 8 |

The anti-anxiety activity of the compounds of the present invention was shown by submitting the compounds to the "benzodiazepine receptors" test. It was recently discovered in fact that there exist specific binding sites for benzodiazepines in the central nervous system which act in mediating the anxiolytic properties of benzodiazepines, and it was demonstrated (see for instance S. Lippa et al., Pharmacol. Biochem. & Behaviour, Vol. 9, 853–856 (1978) and H. Möhler and T. Okada, Brit. J. Psychiat., 133, 261–68 (1978)) that the ability of a substance to displace $^3$H-Diazepam from its specific rat brain receptors is significantly correlated with its anxiolytic properties.

These experiments were carried out by following the method described by H. Möhler and T. Okada in Life Sciences, Vol. 20, 2101–2110 (1977).

The results obtained in these tests with some representative compounds of the present invention are summarized in the following Table B:

TABLE B

| Compound of example No. | In vitro K$_i$ |
| --- | --- |
| 1 | 6.7 × 10$^{-9}$ |
| 2 | 17.2 × 10$^{-9}$ |
| 3 | 1.7 × 10$^{-9}$ |
| 9 | 4.1 × 10$^{-9}$ |
| 10 | 8.1 × 10$^{-9}$ |
| 13 | 36.8 × 10$^{-9}$ |
| 15 | 38.9 × 10$^{-9}$ |
| 16 | 24.6 × 10$^{-9}$ |
| 17 | 23.0 × 10$^{-9}$ |
| 18 | 46.1 × 10$^{-9}$ |

Furthermore some of the compounds of the present invention have been tested in the GABA receptor assay. In this test which was carried out by following the methodology described by M. Herschel and R. J. Baldessarini in Life Sciences, 24, 1849–1854, (1979), the compounds of examples 3 and 15 resulted to be active in displacing more than 50% of $^3$H-GABA from its receptors at micromolar concentrations. In particular the IC$_{50}$ values for the compounds of examples 3 and 15 were 35×10$^{-6}$M and 3×10$^{-6}$M respectively. (As for the GABA's mediating effect of the anxiolytic action of benzodiazepines, see for instance S. J. Enna—Biochemical Pharmacology—30, No. 9, 907–913, (1981)).

The anxiolytic activity of the compounds of the present invention was then confirmed by the results obtained in other experiments in animals. More particularly, the ability of the compounds of the present invention to increase punished responses in a conflict situation, a procedure with high validity for predicting the anxiolytic effect of drugs, was assessed by testing these compounds in rats according to the method described by I. Geller and J. Seifter in Psychopharmacologia 1, 482, (1960). Briefly, in this test, rats are trained to press a lever in order to get a food reward, and each rats exhibits a characteristic and rather stable rate of lever pressing. During an audible signal of a few minutes duration that is occasionally presented, each press of the lever will provide a food reward but will be accompanied by a brief electric shock. A situation of conflict between the rat's desire for food and his fear of the shock soon develops. The rate of lever pressing during the punished period, in the absence of drug treatment, is highly reduced, and each rat develops a characteristic response pattern during the conflict period. The experiments carried out showed that the compounds of the present invention, when administered by the oral route to these trained animals, were able to remarkably increase rat's response during the conflict period at doses which did not influence the characteristic rate of lever pressing during the non-conflict portion.

These favorable pharmacological properties of the compounds of the present invention are accompanied by a low toxicity, as in fact the acute toxicity of the compounds of the present invention is generally higher than 600 mg/kg/i.p.

In view of the above, the use of the compounds of the present invention as anticonvulsant and anti-anxiety agents, is a further specific object of the present invention.

With the term "use" it is intended to refer to all industrially applicable aspects and acts of said use, including the embodiment of the novel compounds into pharmaceutical compositions.

Suitable pharmaceutical compositions contain the novel compounds in admixture or conjunction with organic or inorganic, solid or liquid pharmaceutical excipients and may be employed for enteral and parenteral administration. Suitable excipients are substances that do not react with the new compounds such as for instance, water, gelatin, lactose, starches, magnesium stearate, talcum, vegetable oils, benzyl alcohol, polyalkyleneglycols, or other known medicinal excipients. The new compounds may by administered by various routes: orally, intramuscularly or intravenously, for example. For oral administration the substances are compounded in such forms, as tablets, dispersible powders, capsules, granules, syrups, elixirs and solutions. For intravenous or intramuscular administration the active ingredients are embodied into injectable dosage forms. Such compositions are formulated as known in the art. The dosage regimen for the compounds of the present invention in accord with anticonvulsant, anti-anxiety treatment will depend upon a variety of factors including the particular compound used, the route of administration, and the type of treatment applied for. Good results can be obtained however by administering the compounds of the present invention at a daily dosage range comprised between about 0.1 and about 15 mg/kg preferably in divided doses. It is however clear that a daily dosage beyond the above indicated range may also be employed depending on the individual conditions of the subject to be treated.

Accordingly, the present invention provides a therapeutic composition containing from about 5 to about 500 mg of one of the compounds of the invention as the active ingredient together with a pharmaceutically acceptable carrier.

Following are illustrative pharmaceutical formulations which may be employed in practicing the present invention:

|  | Per tablet |
| --- | --- |
| Preparation of a tablet formulation: | |
| (A) | |
| 5-(2-chlorophenyl)-1,7-dihydro-1,6,7-trimethyl-3-[(2-methyl-1-oxopropyl)oxy]-pyrrolo[3,4-e][1,4]diazepin-2(3H)—one | 50 mg |
| Starch | 25 mg |
| Aerosil ® V200 | 1.25 mg |

|  | Per tablet |
| --- | --- |
| Magnesium stearate | 1.25 mg |
| Lactose | q.s. to 180 mg |
| (B) | |
| 5-(2-chlorophenyl)-1,7-dihydro-3-methoxy-1,6,7-trimethyl-pyrrolo[3,4-][1,4]diazepin-2(3H)—one | 50 mg |
| Starch | 50 mg |
| Aerosil ® V200 | 3 mg |
| Stearic acid | 2 mg |
| Lactose | q.s. to 250 mg |
| Preparation of a capsule formulation | |
| 4-[[[1,7-dihydro-6,7-dimethyl-2-oxo-1-phenyl-3H—pyrrolo[3,4-e][1,4]diazepin-3-yl]-1,4-dioxobutyloxy]amino]butanoic acid ethyl ester hydrochloride | 150 mg |
| Starch | 20 mg |
| Magnesium stearate | 2 mg |
| Lactose | q.s. to 250 mg |

The following examples describe in detail some of the compounds of the invention and illustrate the process for preparing them without limiting the scope of the present invention.

EXAMPLE 1

5-(2-chlorophenyl)-1,7-dihydro-1,6,7-trimethyl-3-(phenylcarbonyloxy)-pyrrolo[3,4-e][1,4]diazepin-2(3H)-one.

A mixture of 5-(2-chlorophenyl)-1,7-dihydro-3-hydroxy-1,6,7-trimethyl-pyrrolo[3,4-e][1,4]diazepin-2(3H)-one (4.75 g, 0.0149 mole), benzoyl chloride (2.45 g, 0.0174 mole) and triethylamine (4.5 g, 0.0445 mole) in benzene (100 ml) is refluxed for about 2 hours. Benzene is then boiled off under vacuum and the residue is taken up with a small amount of water and filtered. The raw material thus obtained is crystallized from ethanol yielding 4.9 g of the compound of the title. M.p. 228°–29° C.

EXAMPLES 2 AND 3

The following compounds are prepared by following substantially the same procedure described in the foregoing example but using the acyl halide indicated between parenthesis instead of benzoyl chloride.

2. 5-(2-chlorophenyl)-1,7-dihydro-1,6,7-trimethyl-3-(2,2-dimethylpropanoyloxy)-pyrrolo[3,4-e][1,4]diazepin-2(3H)-one (from 2,2-dimethylpropanoyl chloride). M.p. 221°–22° C. (crystallized from ethanol).

3. 5-(2-chlorophenyl)-1,7-dihydro-1,6,7-trimethyl-3-(2-methylphenyl)carbonyloxy-pyrrolo[3,4-e][1,4diazepin-2(3H)-one (from 2-methylbenzoyl chloride). M.p. 171°–73° C. (from ethanol).

EXAMPLE 4

1,7-dihydro-6,7-dimethyl-5-phenyl-3-[[4-(1,3-dihydro-1,3-dioxo-2H-isoindol-2-yl)-1-oxobutyl]oxy]-pyrrolo[3,4-e][1,4]diazepin-2(3H)-one 3-[4-(1,3-dihydro-1,3-dioxo-2H-isoindol-2-yl)-1-oxobutyl]chloride (3.8 g, 0.0155 mole) is gradually added to a stirred mixture of 1,7-dihydro-3-hydroxy-6,7-dimethyl-5-phenyl-pyrrolo[3,4-e][1,4]diazepin-2(3H)-one (4 g, 0.0149 mole) and pyridine (40 ml). The reaction mixture is stirred at room temperature for 3 hours, then pyridine is evaporated off under vacuum and the obtained residue is taken up with triethylamine. After boiling off triethylamine under vacuum, the residue is carefully washed with water made alkaline with NaHCO₃. Crystallization of the dried residue from ethanol gives 5 g of the compound of the title. M.p. 210°–12° C.

EXAMPLES 5 TO 11

The following compounds are prepared by following the same procedure described in example 4 but starting from the compounds indicated between parenthesis.

5. 3-[(4-fluorobenzoyl)oxy)]-1,7-dihydro-6,7-dimethyl-5-phenyl-pyrrolo[3,4-e][1,4]diazepin-2(3H)-one (from 1,7-dihydro-3-hydroxy-6,7-dimethyl-5-phenyl-pyrrolo[3,4-e][1,4]diazepin-2(3H)-one and (4-fluorobenzoyl)chloride). M.p. 211°–13° C. (from ethanol)

6. 1,7-dihydro-6,7-dimethyl-3-[[4-(1,1-dimethylethyl)-benzoyl]oxy]-5-phenyl-pyrrolo[3,4-e][1,4]diazepin-2(3H)-one (from 1,7-dihydro-3-hydroxy-6,7-dimethyl-5-phenyl-pyrrolo[3,4-e][1,4]diazepin-2(3H)-one and [4-(1,1-dimethylethyl)benzoyl]chloride). M.p. 235°–37° C. (from isopropanol)

7. 3-[(cyclohexylcarbonyl)oxy]-1,7-dihydro-6,7-dimethyl-5-phenyl-pyrrolo[3,4-e][1,4]diazepin-2(3H)-one (from 1,7-dihydro-3-hydroxy-6,7-dimethyl-5-phenyl-pyrrolo[3,4-e][1,4]diazepin-2(3H)-one and cyclohexylcarbonyl chloride). M.p. 209°–10° C. (from isopropanol)

8. 1,7-dihydro-6,7-dimethyl-3-[(1-oxobutyl)oxy]-5-phenyl-pyrrolo[3,4-e][1,4]diazepin-2(3H)-one (from 1,7-dihydro-3-hydroxy-6,7-dimethyl-5-phenyl-pyrrolo[3,4-e][1,4]diazepin-2(3H)-one and 1-oxobutyl chloride). M.p. 198°–200° C. (from isopropanol).

9. 5-(2-chlorophenyl)-1,7-dihydro-1,6,7-trimethyl-3-[(2-methyl-1-oxopropyl)oxy]-pyrrolo[3,4-e][1,4]diazepin-2(3H)-one (from 5-(2-chlorophenyl)-1,7-dihydro-3-hydroxy-1,6,7-trimethyl-pyrrolo[3,4-e][1,4]diazepin-2(3H)-one and (2-methyl-1-oxopropyl)chloride). M.p. 173°–5° C. (from ethanol).

10. 5-(2-chlorophenyl)-1,7-dihydro-3[(4-methoxy-benzoyl)oxy]-1,6,7-trimethyl-pyrrolo[3,4-e][1,4diazepin-2(3H)-one (from 5-(2-chlorophenyl)-1,7-dihydro-3-hydroxy-1,6,7-trimethylpyrrolo[3,4-e][1,4-diazepin-2(3H)-one and (4-methoxybenzoyl)chloride). M.p. 138°–40° C. (from ethanol).

11. 5-(2-chlorophenyl)-3-[[1,1-biphenyl-4-yl)carbonyl]oxy]-1,7-dihydro-1,6,7-trimethyl-pyrrolo[3,4-e][1,4]diazepin-2(3H)-one (from 5-(2-chlorophenyl)-1,7-dihydro-3-hydroxy-1,6,7-trimethyl-pyrrolo[3,4-e][1,4]diazepin-2(3H)-one and [(1,1-biphenyl-4-yl)carbonyl]chloride). The raw material is purified by column chromatography eluting with a mixture chloroform/methanol 99/1. M.p. 173°–5° C.

EXAMPLE 12

3-decanoyloxy-1,7-dihydro-6,7-dimethyl-5-phenyl-pyrrolo[3,4-e][1,4]diazepin-2(3H)-one A mixture of 1,7-dihydro-3-hydroxy-6,7-dimethyl-5-phenyl-pyrrolo[3,4-e][1,4]diazepin-2-(3H)-one (4 g, 0.0149 mole) and decanoyl chloride (3 g, 0.0157 mole) in pyridine (40 ml) is heated for two hours at 60°–70° C. Pyridine is then evaporated off under vacuum and the oily residue it taken up with ethyl ether. After 24 hours, the product which solidifies is recovered by filtration and washed with ethyl ether. It is then triturated with a small amount of water, filtered again and dried under vacuum at 40° C. yielding 3.6 g of the compound of the title. M.p. 187°–88° C. (from ethanol).

EXAMPLES 13 AND 14

The following compounds are prepared by following the same procedure of example 12 but using the starting materials indicated between parenthesis.

13. 1,4-butandioic acid 1-[5-(2-chlorophenyl)-1,3,7-trihydro-1,6,7-trimethyl-2-oxo-pyrrolo[3,4-e][1,4]diazepinyl]ester (from 5-(2-chlorophenyl)-1,7-dihydro-3-hydroxy-1,6,7-trimethyl-pyrrolo[3,4-e][1,4]diazepin-2(3H)-one and succinic anhydride). M.p. 173°-75° C. (from isopropanol)
14. 1,4-butandioic acid 1-[1,3,7-trihydro-6,7-dimethyl-2-oxo-5-phenyl-pyrrol[3,4-e][1,4]diazepinyl]ester (from 1,7-dihydro-3-hydroxy-6,7-dimethyl-5-phenyl-pyrrolo[3,4-e][1,4]diazepin-2(3H)-one and succinic anhydride). M.p. 153°-55° C. (from ethanol)

EXAMPLE 15

4-[[[1,7-dihydro-6,7-dimethyl-2-oxo-1-phenyl-3H-pyrrolo[3,4-e][1,4]diazepin-3-yl]-1,4-dioxobutyloxy]amino]butanoic acid ethyl ester hydrochloride A solution of ethyl chlorocarbonate (1.6 g) in chloroform (10 ml) is dripped into a mixture of the compound of example 14 (3.2 g, 0.0087 mole) and triethylamine (2.8 ml) in chloroform (90 ml) cooled to 0° C. After stirring at 0° C. for 20 minutes, a further amount of triethylamine (2 ml) is added dropwise to the reaction mixture, then γ-aminobutyric acid ethyl ester (2.8 g, 0.0213 mole) is gradually added. The obtained reaction mixture is allowed to warm to room temperature under stirring and is then refluxed for 30 minutes. The solvent is evaporated off and the residue is taken up with water acidified with HCl. The aqueous solution is extracted with ethyl ether, made alkaline with NaHCO$_3$ and extracted again with chloroform. The chloroform solution is dried over Na$_2$SO$_4$, filtered and concentrated to dryness giving a raw residue (6 g) which is purified by silicagel column chromatography eluting with chloroform/methanol 98/2. The purified product thus obtained (2.3 g) is taken up with acetone (70 ml) acidified with HCl/ether and slightly heated to complete solution. The product which crystallizes upon standing at room temperature is recovered by filtration yielding 2.1 g of the compound of the title.
M.p. 125°-7° C.

EXAMPLE 16

5-(2-chlorophenyl)-3-ethoxy-1,7-dihydro-1,6,7-trimethyl-pyrrolo[3,4-e][1,4]diazepin-2(3H)-one hydrochloride hydrate A solution of 5-(2-chlorophenyl)-1,7-dihydro-3-hydroxy-1,6,7-trimethylpyrrolo[3,4-e][1,4]diazepin-2(3H)-one (10 g, 0.0315 mole) in thionyl chloride (30 ml) is allowed to stand at room temperature overnight and is then concentrated to dryness under vacuum. The residue is triturated with ethyl ether and concentrated again to dryness in order to remove thionyl chloride.

The obtained residue is taken up with ethanol (60 ml) and allowed to stand at room temperature for 3 hours. After evaporating the solvent, the residue is taken up with water, made alkaline with NaHCO$_3$ and extracted with chloroform. The chloroform solution is dried over Na$_2$SO$_4$, filtered and concentrated to dryness giving 7 g of a raw product which is purified by silicagel column chromatography eluting with chloroform/methanol 98/2. The purified product is then dissolved in hot ethyl ether and HCl in ether is added to precipitate the compound of the title. M.p. 110°-1° C.

EXAMPLE 17

5-(2-chlorophenyl)-1,7-dihydro-3-methoxy-1,6,7-trimethyl-pyrrolo[3,4-e][1,4]diazepin-2(3H)-one hydrochloride hydrate The compound of the title is prepared by following essentially the same procedure of the foregoing example but using methanol instead of ethanol. M.p. 101°-3° C.

EXAMPLE 18

5-(2-chlorophenyl)-3-[[3-(ethoxycarbonyl)propyl]amino]-1,7-dihydro-1,6,7-trimethyl-pyrrolo[3,4-e][1,4]diazepin-2(3H)-one A mixture of 5-(2-chlorophenyl)-1,7-dihydro-3-hydroxy-1,6,7-trimethyl-pyrrolo[3,4-e][1,4]diazepin-2(3H)-one (6.3 g, 0.0198 mole) and thionyl chloride (18 mole) is allowed to stand at room temperature for one night. The 3-chloro derivative which forms is precipitated by the addition of ethyl ether, recovered by filtration and washed on filter with ethyl ether. The obtained intermediate is dissolved in chloroform (100 ml) and triethylamine (8 g) and γ-aminobutyric acid ethyl ester hydrochloride (6.4 g, 0.0382 mole) are gradually added to the obtained solution. The reaction mixture is allowed to stand, at room temperature for one day, then chloroform is evaporated, the residue is taken up with water acidified with HCl and the undissolved oil is extracted with chloroform. The chloroform solution is neutralized by washing with aqueous NaHCO$_3$, dried over Na$_2$SO$_4$, filtered and concentrated to dryness yielding 6 g of an oily residue.

This raw residue is purified by silicagel column chromatography eluting with chloroform containing 1% methanol. The purified product is then triturated with ethyl ether and crystallized from isopropanol/ether giving 0.65 g of the compound of the title. M.p. 105°-7° C.

PREPARATION OF THE STARTING COMPOUNDS OF FORMULA II (A)

1,7-Dihydro-3-hydroxy-6,7-dimethyl-5-phenyl-pyrolo[3,4-e][1,4]diazepin-2(3H)-one (a) N-(4-benzoyl-5-methyl-(1H)pyrrol-3-yl) 2-chloroacetamide Aminoacetonitrile (0.04 mole) and benzoyl acetone (0.04 mole) were refluxed for four hours in 30 ml of anhydrous benzene in the presence of 100 mg of p-toluenesulfonic acid. After cooling the reaction mixture was filtered and the solvent was evaporated to give a residue (m.p. 110°-11° C.) which was dissolved in an ethanol solution containing sodium ethoxide (0.041 mole). The mixture was allowed to stand for 72 hours at 6° C. and acidified with HCl gas and the solid precipitate which forms, 4-amino-3-benzoyl-2-methylpyrrole hydrohalide, was recovered by filtration.

4-Amino-3-benzoyl-2-methylpyrrole hydrochloride (0.019 mole) was dissolved in water (40 ml) and the solution was treated with charcoal (0.1 g) and filtered. Toluene was added and chloroacetylchloride (0.067 mole) and aqueous NaOH (58.1 ml, 20% w/v) were added separately but simultaneously during 1 hour to the stirred two-phase solution. The reaction mixture was maintained under an inert atmosphere and at room temperature for 1.5 hour. The compound of the title which spontaneously crystallized out of the reaction mixture, was collected by filtration.

(b) N-(4-benzoyl-1,5-dimethyl-(1H)-pyrrol-3-yl) 2-chloroacetamide

N-(4-benzoyl-5-methyl(1H)-pyrrol-3-yl)2-chloroacetamide (0.019 mole) was dissolved in butan-2-one (60 ml) and $K_2CO_3$ (4.5 g) and dimethylsulphate (0.037 mole) were added to the obtained solution. The reaction mixture was maintained at the reflux temperature for 5 hours and at room temperature overnight. An inert atmosphere was maintained throughout the process. The inorganic salts were filtered and the clear solution was evaporated under vacuum to yield a residue which upon crystallization from methanol gave the compound of the title.

(c) N-(4-benzoyl-1,5-dimethyl(1H)pyrrol-3-yl)2-iodoacetamide

N-(4-benzoyl-1,5-dimethyl(1H)pyrrol-3-yl)2-chloroacetamide (0.741 mole) and potassium iodide (1.62 mole) were refluxed in ethanol (3400 ml) for 5 hours with stirring. The reaction mixture was then cooled, the inorganic salts were filtered and the solvent was evaporated under vacuum. The obtained residue was purified by washing first with water and then with cold ethanol. M.p. 135°–137° C. Yield 87%.

(d) N-(4-benzoyl-1,5-dimethyl(1H)pyrrol-3-yl)-2-hydroxylaminoacetamide

Sodium hydroxide (64 g) was added to a solution of hydroxylamine hydrochloride (111 g) in water (370 ml) and the obtained solution was diluted with ethanol (3500 ml). N-(4-benzoyl-1,5-dimethyl(1H)pyrrol-3-yl)-2-iodoacetamide (124.5 g) was then added and the obtained suspension was stirred under nitrogen stream for about 48 hours. The reaction mixture was filtered in order to remove the salts and the filtrate was concentrated to dryness at the pump. The residue was washed with a small amount of water and crystallized from ethyl acetate yielding 82.5 g of the compound of the title. M.p. 140°–42° C.

(e) 1,7-dihydro-6,7-dimethyl-5-phenyl-pyrrole[3,4-e][1,4]diazepin-2(3H)-one-4-oxide First step: Preparation of the intermediate 1,2,3,7-tetrahydro-4-hydroxy-6,7-dimethyl-2-oxo-5-phenyl-pyrrolo[3,4-e][1,4]diazepinium chloride The compound obtained in step (d) above (79.4 g) was suspended in isopropanol containing 2.1% of HCl (3700 ml) and refluxed for 2 hours with stirring. The reaction mixture was then cooled to 0° C. and a first crop (61 g) of the compound of the title which crystallized out was recovered by filtration. A second step crop (9 g) was obtained by concentrating the mother liquors to a small volume. M.p. 220°–223° C. with decomposition.

Second step: Conversion of the diazepinium salt to N-oxide.

The diazepinium chloride (140 g) was dissolved in water (1400 ml), the obtained solution was cleared by filtration and brought to pH 9 by the addition of $Na_2CO_3$ with stirring. NaCl (400 g) was then added to the suspension, and stirring was continued for further 60 minutes. The compound of the title which precipitated was then recovered by filtration (113 g). M.p. 225°–258° C.

(f) 3-Acetoxy-1,7-dihydro-6,7-dimethyl-5-phenyl-pyrrolo[3,4-e][1,4]diazepin-2(3H)-one The compound obtained above was suspended in acetic anhydride (500 ml) and the temperature of the reaction raised to 75° C. in a few minutes. The reaction mixture was heated to 85° C. for 20 minutes with stirring then it was cooled to 0° C. and the crystalline precipitate was recovered yielding 117 g of the compound of the title. M.p. 255°–56° C.

(g) 1,7-Dihydro-3-hydroxy-6,7-dimethyl-5-phenylpyrrolo[3,4-e][1,4]diazepin-2(3H)-one To a suspension of 3-acetoxy-1,7-dihydro-6,7-dimethyl-5-phenyl-pyrrolo[3,4-e][1,4]diazepin-2(3H)-one (40 g) in ethanol (2000 ml), cooled to 5° C., 1N NaOH (128 ml) was added with stirring. After 10 minutes the reaction mixture was cooled to about 4° C. and allowed to stand at this temperature for one night. Then $CO_2$ was gradually added to the solution to lower the pH to about 8. Ethanol was evaporated at the pump and the obtained residue was washed first with water and then with methanol, and crystallized from ethanol yielding 30 g of the compound of the title. M.p. 243° C. with decompostion.

(B) 5-(2-chlorophenyl)-1,7-dihydro-3-hydroxy-1,6,7-trimethylpyrrolo[3,4-e][1,4]diazepin-2(3H)-one (a) N-[4-(2-chlorobenzoyl)-1,5-dimethyl-(1H)pyrrol-3-yl]-2-iodoacetamide This compound was prepared by following the procedures described in example (A), steps (a), (b), and (c) but starting from (2-chlorobenzoyl)acetone instead of benzoylacetone. M.p. 155°–57° C.

(b) N-[4-(2-chlorobenzoyl)-1,5-dimethyl(1H)pyrrol-3-yl]2-hydroxylaminoacetamide

The compound of the title was prepared by following essentially the procedures described in example (A) step (d) but prolonging the reaction time to 72 hours. The compound of the title was then recovered by diluting the reaction mixture with water (5 times the initial volume) containing NaCl (5.5 kg) and filtering the precipitate which crystallized M.p. 166°–68° C. with decomposition.

(c) 5-(2-chlorophenyl)-1,7-dihydro-6,7-dimethylpyrrolo[3,4-e][1,4]diazepin-2(3H)-one-4-oxide A suspension of N-[4-(2-chlorobenzoyl)-1,5-dimethyl(1H)-pyrrol-3-yl]2-hyroxylaminoacetamide (130 g) in a solution of sulfuric acid (250 ml) in water (2400 ml) was heated to 80° C. for 1 hour. The reaction mixture was cooled to 20° C., cleared by filtration, diluted with water (1500 ml) and filtered again. The acidic solution was then cautiously made alkaline by the addition of $Na_2CO_3$ and extracted with chloroform. By concentrating the organic extracts to dryness under vacuum at room temperature, 80 g of the compound of the title were recovered.

(d) 5-(2-chlorophenyl)-1,7-dihydro-1,6,7-trimethylpyrrolo[3,4-e][1,4]diazepin-2(3H)-one-4-oxide A solution of NaOH (27 g) in water (4700) was added with stirring to 5-(2-chlorophenyl)-1,7-dihydro-6,7-dimethylpyrrolo[3,4-e][1,4]diazepin-2(3H)-one-4-oxide (165 g) finely suspended in ethanol (940 ml).

Then, dimethylsulfate (54.7 ml) was added during 10 minutes keeping the temperature at about 20° C. The reaction mixture was stirred at this temperature for 2 hours, then the insoluble material was separated by under vacuum filtration. The clear solution was salted with NaCl and extracted with chloroform. The organic extract was dried over $Na_2SO_4$, and concentrated to dryness under vacuum at 25°–30° C. The residue was washed with ethyl ether yielding 135 g of the compound of the title. M.p. 198°–200° C. (from isopropanol).

(e) 3-Acetoxy-5-(2-chlorophenyl)-1,7-dihydro-1,6,7-trimethylpyrrolo[3,4-e][1,4]diazepin-2(3H)-one The compound obtained in step (d) above was suspended in acetic anhydride (660 ml) and the reaction flask was heated in a water-bath at 55° C. After stirring for 15 minutes the reaction mixture was concentrated to dryness under vacuum, and the obtained residue was taken up with boiling ethanol and treated with charcoal. By concentrating to a volume of 600 ml and cooling, the compound of the title (103 g) crystallized. M.p. 202°–4° C.

(f) 5-(2-chlorophenyl)-1,7-dihydro-3-hydroxy-1,6,7-trimethylpyrrolo[3,4-e][1,4]diazepin-2(3H)-one 1N NaOH (557 ml) was added to a suspension of 3-acetoxy-5-(2-chlorophenyl)-1,7-dihydro-1,6,7-trimethylpyrrolo-[3,4-e][,4]diazepin-2(3H)-one (200 g) in ethanol (1500 ml) keeping the temperature between 0° and 5° C. After stirring at 5° C. for 1 hour the suspension was gradually poured into a solution of NaCl (2 kg) in water (7500 ml), and the precipitate which formed was recovered by under vacuum filtration and washed first with water, and then with cold methanol yielding 160 g of the compound of the title. Further 17 g were obtained by extracting the filtrate with ethyl acetate and evaporating the extracting solvent.

M.p. 182°–83° C. (from ethyl acetate).

We claim:

1. A 1,7-dihydro-pyrrolo[3,4-e][1,4]diazepin-2-(3H)-one of following formula I

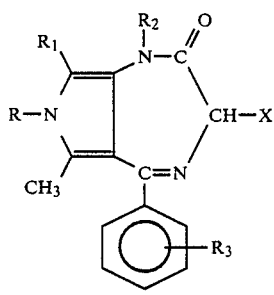

wherein

R represents methyl, ethyl, propyl, 1-methylethyl, butyl, 1-methylpropyl, 2-methylpropyl and 1,1-dimethylethyl $R_1$ stands for hydrogen, methyl, ethyl, phenyl, chloro, bromo or nitro $R_2$ is hydrogen, methyl, ethyl, propyl, 1-methylethyl, butyl, 1-methylpropyl, 2-methylpropyl and 1,1-dimethylethyl $R_3$ represents hydrogen, chloro, fluoro, bromo, trifluoromethyl and methoxy, and X is

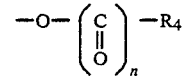

or $-NH-R_4$ wherein n is 0 or 1 and $R_4$ represents a straight or branched alkyl or alkenyl group which may contain up to 12 carbon atoms, which may be unsubstituted or substituted with one or more groups independently selected from ($C_{1-4}$)alkoxy, halogen, carboxy, carbo-($C_{1-4}$)alkoxy, amino, mono- or di-($C_{1-4}$)alkylamino, ($C_{2-4}$)alkanoylamino, benzoylamino, phthalimido, carbamyl, ($C_{1-4}$)alkylcarbamyl, carboxy-($C_{1-4}$)alkylcarbamyl, carbalkoxy-($C_{1-4}$)alkylcarbamyl, and phenylcarbamyl, a ($C_{5-8}$)cycloalkyl group which may be unsubstituted or substituted with one or two groups independently selected from ($C_{1-4}$)alkyl, hydroxy, halogen, carboxy, and carbo-($C_{1-4}$)alkoxy, or a phenyl group which may be unsubstituted or substituted with 1 to 3 groups independently selected from ($C_{1-4}$)alkyl, hydroxy, halogen, carboxy, and carbo($C_{1-4}$)alkoxy, or a phenyl group which may be unsubstituted or substituted with 1 to 3 groups independently selected from ($C_{1-4}$)alkyl, ($C_{1-4}$)alkoxy, ($C_{3-8}$)cycloalkyl, amino, mono- or di-($C_{1-4}$)alkylamino, phenyl, trifluoromethyl and halogen with the proviso that when simultaneously $R_1$ is hydrogen, methyl, ethyl or phenyl and X is an

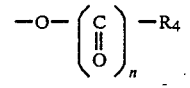

group wherein n is 1, $R_4$ cannot represent methyl; and the pharmaceutically acceptable acid addition salts thereof.

2. A compound according to claim 1 wherein R is methyl, $R_1$ is hydrogen, and $R_3$ represents hydrogen, chloro, fluoro or bromo.

3. A compound according to claim 1 wherein R is methyl, $R_1$ is hydrogen, $R_2$ is hydrogen or methyl and $R_3$ stands for hydrogen or chloro.

4. A compound according to claim 1 which is 5-(2-chlorophenyl)-1,7-dihydro-1,6,7-trimethyl-3-[(2-methyl-1-oxopropyl)oxy]pyrrolo[3,4-e][1,4]diazepin-2(3H)-one.

5. A process for preparing a compound according to claim 1 which comprises:

(a) when a compound of formula I is desired wherein R, $R_2$ and $R_3$ are as defined in claim 1, $R_1$ is hydrogen, methyl, ethyl or phenyl and X is an

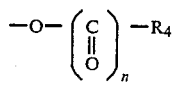

group wherein n is 1, acylating the corresponding 3-hydroxy derivative of formula II

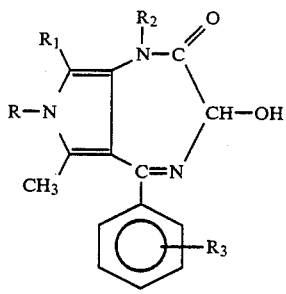

wherein R, $R_2$ and $R_3$ are as defined above and $R_1$ is hydrogen, methyl, ethyl or phenyl with an acyl halide or anhydride of formula

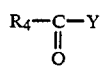

wherein $R_4$ is as defined in claim 1 and Y is a halogen atom or the group

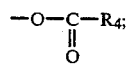

(b) when a compound of formula I is desired wherein R, $R_2$ and $R_3$ are as defined in claim 1, $R_1$ is hydrogen, methyl, ethyl or phenyl and X is an

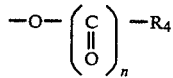

or —NH—$R_4$ group wherein n is zero, transforming the corresponding 3-hydroxy derivative of formula II into the corresponding 3-chloro derivative through reaction with an inorganic acid chloride and then replacing the 3-chloro atom with an —$OR_4$ or —$NHR_4$ group by reaction with a compound of formula $HOR_4$ or $H_2NR_4$;

(c) when a compound of formula I is desired wherein R, $R_2$, $R_3$, and X are as defined in claim 1 and $R_1$ is chloro, bromo, or nitro, submitting the corresponding compound of formula I wherein $R_1$ is hydrogen, obtained according to (a) or (b) above, to common chlorination, bromination or nitration procedures;

said process being further characterized in that when a compound of formula I is desired wherein R, $R_1$, $R_2$, and $R_3$ are as defined in claim 1 and X is an

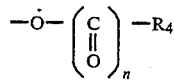

group wherein n is 1 and $R_4$ is a straight or branched alkyl or alkenyl radical substituted at the 2- or 3-position with a carboxy, carbo-($C_{1-4}$)alkoxy, carbamyl, ($C_{1-4}$)alkylcarbamyl, carboxy-($C_{1-4}$)alkylcarbamyl, carbo-($C_{1-4}$)alkoxy-($C_{1-4}$)alkylcarbamyl or phenylcarbamyl, a suitably selected cyclic anhydride is employed and, if desired, the free carboxy group of this obtained compound of formula I is then transformed into a carbalkoxy, carbamyl, or substituted carbamyl group as seen above, by conventional esterification or amination procedures.

6. A process as in claim 5 for preparing a compound of formula I wherein R is methyl, $R_1$ is hydrogen, $R_2$ is hydrogen, methyl, ethyl, propyl, 1-methylethyl, butyl, 1-methylpropyl, 2-methylpropyl and 1,1-dimethylethyl and $R_3$ represents hydrogen, chloro, fluoro or bromo.

7. A process as in claim 5 for preparing a compound of formula I wherein R is methyl, $R_1$ is hydrogen, $R_2$ is hydrogen or methyl and $R_3$ stands for hydrogen or chloro.

8. A method of treating anxiety or convulsions by the administration of an anti-anxiety or anticonvulsant amount of a compound of claim 1 to a patient in need thereof.

9. A composition useful for treating anxiety of convulsions comprising an amount of a compound of claim 1 effective for treating anxiety of convulsions in combination with a pharmaceutically acceptable carrier.

10. A pharmaceutical composition containing from about 5 to about 500 mg of a compound of claim 1 as the active ingredient together with a pharmaceutically acceptable carrier.

* * * * *